United States Patent [19]
Alvarez

[11] Patent Number: 5,221,843
[45] Date of Patent: Jun. 22, 1993

[54] ACTIVE ENERGY SELECTIVE X-RAY IMAGE DETECTION

[76] Inventor: Robert E. Alvarez, 2369 Laura La., Mountain View, Calif. 94043

[21] Appl. No.: 872,788

[22] Filed: Apr. 23, 1992

[51] Int. Cl.⁵ .................... G01N 23/04; G03B 42/02
[52] U.S. Cl. ................... 250/327.2; 250/484.1; 250/486.1; 250/487.1; 378/185
[58] Field of Search ............ 250/327.2, 484.1, 487.1, 250/486.1; 378/174, 162, 185

[56] References Cited

U.S. PATENT DOCUMENTS

| | | | |
|---|---|---|---|
| 3,859,527 | 1/1975 | Luckey | 250/327.2 |
| 4,029,963 | 6/1977 | Alvarez et al. | 250/367 |
| 4,413,353 | 11/1983 | Macovski et al. | 378/62 |
| 4,511,799 | 4/1985 | Bjorkholm | 250/367 |
| 4,578,803 | 3/1986 | Macovski | 378/62 |
| 4,626,688 | 12/1986 | Barnes | 250/361 |
| 4,855,598 | 8/1989 | Ohgoda et al. | 250/327.2 |
| 4,975,590 | 12/1990 | Tanaka | 378/185 |

FOREIGN PATENT DOCUMENTS

| | | | |
|---|---|---|---|
| 585470 | 12/1977 | U.S.S.R. | 378/185 |
| 1154973 | 1/1969 | United Kingdom . | |

OTHER PUBLICATIONS

Alvarez, R. E. and A. Macovski "Energy Selective . . ." Phys. Med. Biol. vol. 21, pp. 733-744, 1976.
Low, W., J. T. Steinberger, and E. A. Braun "The effect of alternating . . ." Journal of the Optical Society of America, vol. 44, pp. 504-505 1954.
Steinberger, I. T., E. A. Braun and E. Alexander, "Gudden-Pohl and Memory . . . " J. Phys. Chem. Solids, vol. 3, pp. 133-140, 1957.

*Primary Examiner*—Carolyn E. Fields

[57] ABSTRACT

An apparatus and method for energy selective x-ray image detection. A source produces two fluxes of x-ray radiation with two different energy spectra. The fluxes are sequentially incident on the subject then on two layered planar detectors with control means. Examples of planar detectors are stimulable phosphor screens or intensifying screen/photographic film detectors. Examples of control means are visible light sources or electric generators with stimulable phosphor screens or light valves with intensifying screen/film detectors. A sequencer uses control means to selectively enhance the response of a predetermined detector to corresponding sequential radiation flux. The predetermined response can be chosen to enhance the inherent energy selectivity of the layered detector e.g. the first detector preferentially responds to low energy while the second detector preferentially responds to high energy x-ray photons. Planar detectors are used so that the layered detector fits in a cassette compatible with film cassettes used in medical radiography.

12 Claims, 3 Drawing Sheets

ACTIVE ENERGY SELECTIVE X-RAY IMAGE DETECTION

BACKGROUND

1. Field of Invention

This invention relates to radiography. In a primary application the invention relates to the detection of images of x-ray flux with different energy spectra.

2. Description of Prior Art

Conventional radiography not only projects three dimensional body structures onto a two dimensional image but also integrates the transmission over a broad spectrum of x-ray photon energies. The projection over space and integration over the energy spectrum result in a superposition of all tissues and materials in the image making it difficult to visualize many structures of interest. For example, tumors and other soft tissue materials are often obscured by overlying bone. Also, large amounts of iodine containing contrast agents must be administered into blood vessels to make them visible in the presence of other body structures.

A solution to this problem lies in the physical fact that different materials have attenuation coefficients which have unique functions of energy. By making measurements at different regions of the energy spectrum, and combining them in an appropriate image processing system, specific materials can be removed or isolated. A preferred approach to the use of the energy spectrum information is described in U.S. Pat. No. 4,029,963 (1977), "X-ray Spectral Decomposition Imaging System," issued to R. E. Alvarez and A. Macovski. Here measurements made at two different regions of the x-ray energy spectrum are processed to calculate the photoelectric and Compton scattering components of the attenuation. These components, representing essentially atomic number and density, can be combined to represent different materials such as bone or soft tissue.

The performance of systems utilizing energy spectrum information depends critically on the energy selective measurements. In medical imaging systems, the important factor to consider is the noise for a given patient dose. Lower noise means that more subtle differences and structures can be discerned in the images. Patient dose should always be minimized in medical examinations. Noise and dose in processed energy spectrum images were studied by R. E. Alvarez and A. Macovski in their paper "Energy selective reconstructions in x-ray computerized tomography", Physics in Medicine and Biology, 1976, Vol. 21, pp. 733-744. They showed that the noise decreases with increased dose and with increased difference in average energies of the measurements. A larger difference in average energies produces lower noise for the same dose.

Approaches to energy selective measurement can be divided into two broad classes. In one class, the energy spectrum of the source is varied and the flux transmitted through the subject is measured with conventional, non-energy selective detectors. In the other class, the detectors themselves have energy selective capability to separate the transmitted photons into different effective spectra. The source spectrum can be changed, for example, by switching the voltage of an x-ray tube or by passing the x-ray beam through different x-ray attenuators. An example of an energy selective detector is a counting detector with pulse height analysis. Counting detectors are not practical in x-ray transmission medical imaging systems because the counting rates are too high. Other approaches need to be used with these systems.

An important consideration in choosing x-ray detectors is that, by far, the largest number of medical examinations are done with projection radiography utilizing area detector systems such as film. Other possible detectors are image intensifier tubes and scanned line detectors. Image intensifier tubes are used in medical radiography for special procedures requiring real time imaging of motion. Examples would be the motion of contrast agents though the circulatory system or the intestine. The image intensifier tubes have large vacuum envelopes. They are expensive and require complex mechanical support systems. Therefore they are not used in general radiography but only where real time imaging is indispensable. Scanned line detectors use linear electronic detector arrays to acquire an image by scanning it one line at a time. Line detectors have not been commercially accepted for several reasons. Freezing of motion requires that images be acquired in a short time resulting in high scan rates. These high rates produce stringent requirements on the electronics and the mechanical system. They also require much higher x-ray tube output than area detectors since they use only a small fraction of the tube's flux. Finally, scanned line detectors are not mechanically compatible with conventional x-ray equipment used for general radiography. Neither image intensifier tubes nor scanned line detectors are good choices for energy selective imaging in general radiography.

During medical examinations, film is placed in a thin protective box called a cassette. Nearly all medical equipment is designed to be used with these cassettes. If a detector can not fit into cassette holders, it would require special purpose systems that would be inconvenient for medical institutions. This would limit the market so compatibility with film cassette holders is a highly desirable feature of detectors for energy selective measurements.

Changing the source spectrum can provide energy selective measurements with conventional non-energy selective area detectors. To reduce image blur due to motion of the patient and body structures, both measurements must be made within a small fraction of a second (say about 0.1 second). Modern x-ray power supplies are controlled electronically by microprocessors so voltage switching in this period of time is relatively easy. It is also easy to change a small attenuator at the tube this rapidly. But making measurements within this time period with conventional area detectors has been difficult. Each spectral measurement must be recorded on a separate sheet. The only way to make separate measurements has been to physically move each sheet in and out of the path of the x-rays. These sheets are large, 35 cm by 43 cm for typical examinations, so mechanically moving them in this short a time is very difficult. Also, a mechanical changer does not fit into cassette holders of existing medical x-ray equipment.

U.S. Pat. No. 4,029,963 cited above describes an energy selective area detector, the passive layered detector cassette. The cassette consists of two conventional area detectors arranged in two layers so that x-rays forming the images pass first through a front detector then to a second back detector. The energy selectivity is provided by the x-ray filtering of the materials in the detectors. Since attenuation decreases with x-ray energy (except at a few discrete absorption edges) the mean distance before absorption is smaller for low energy than for high energy photons. Thus, the lower energies are preferentially absorbed in the front detector while the higher energies are preferentially absorbed in the back detector. If the material has an absorption edge within the energy region of interest, the opposite can be true. In this case the attenuation increases with energy so the photons detected by the front screen have a higher average energy than the those detected by the back screen.

In either case, the passive layered detector cassette has several important advantages. First, it works completely passively without any motion of the area detectors. A single exposure creates the energy selective images in both detectors simultaneously so there is no problem with motion. Another advantage is that the cassette has approximately the same size as an ordinary cassette. Thus it can be used in conventional x-ray equipment. Also, the approach can be used with any area detector.

The passive layered approach, however, has severe problems with selectivity compared to x-ray source spectrum switching. It must rely on the physical properties of x-ray attenuation to separate x-ray photons into different spectra. The paper by Alvarez and Macocski cited above shows the attenuation coefficient functions depend only on two constants and and, for some materials, on absorption edge energies. There are a very limited variety of attenuation functions and they are not especially suitable for selectivity. The problem is particularly difficult with detectors where only a small number of detector materials are in widespread commercial use. In order to enhance selectivity, materials with different atomic numbers should be used in the front and back layers. With different atomic number detector materials, layered detectors have poor selectivity. With only one material for both front and back screens, their selectivity is substantially worse.

U.S. Pat. No. 4,511,799 (1985) issued to P. J. Bjorkholm describes a passive layered cassette in which the x-ray beam is not perpendicular to the surface of the detectors. The only difference with the previous approach is that the path length is now the slant distance through the detector. The same attenuation can be obtained in a perpendicular incidence approach simply by using a thicker detector. Thus the non-perpendicular incidence angle does not increase the selectivity of the detector. The patent also describes the use of gas detectors. Gases have the same physical attenuation functions as solids only lower density. A solid detector can have the same x-ray attenuation as a gas if it is thin enough. A gas detector, therefore does not have inherently different energy selectivity than a solid detector.

U. K. Pat. No. 1,154,973 (1969) issued to W. K. French and E. W. Bauer, U.S. Pat. No. 4,578,803 (1986) issued to A. Macovski, and U.S. Pat. No. 4,626,688 (1986) issued to G. T. Barnes describe passive layered cassettes with an absorbing layer between the front and back detector. This can increase selectivity somewhat by absorbing low energy photons, that pass through the front detector, before they reach the back detector. Unfortunately, the absorbing layer also attenuates high energy photons so it can increase the required patient dose. The attenuation coefficient funtion of the absorber is also limited to the same set of physically realizable functions as the detectors. Its capability to increase selectivity is therefore limited.

U.S. Pat. No. 4,855,598 (1989) issued to M. Ohgoda and N. Nakajima describes a passive layered cassette with multiple detector layers. The paper by Alvarez and Macovski cited above shows that two spectrum measurements are sufficient to extract complete energy dependent information. Adding measurements does not add any new information. If the extra measurements are summed before processing then the result is the same as using thicker detectors in the approach of U.S. Pat. No. 4,029,963 since x-ray detectors are linear. If the data from the extra detectors are not used, the result is the same as using an absorbing layer.

OBJECTS AND ADVANTAGES

Accordingly, several objects and advantages of the present invention are:

(a) to provide an energy selective area x-ray image detector system with better x-ray energy selectivity than either source spectrum switching or a passive layered cassette;

(b) to provide an energy selective area x-ray image detector system producing the enhanced selectivity of source spectrum switching but without mechanical motion of the detectors;

(c) to provide an energy selective area x-ray image detector system that can acquire several images with different spectra in a small fraction of a second;

(d) to provide an energy selective area x-ray image detector system whose dimensions are similar to ordinary x-ray film cassettes so it can fit into cassette holders of conventional x-ray equipment.

Still further objects and advantages will become apparent from a consideration of the ensuing description and drawings.

DRAWING FIGURES

In the drawings, closely related figures have the same number but different alphabetic suffixes.

REFERENCE NUMERALS IN DRAWINGS

| | |
|---|---|
| 10,10',10" Active Cassette | 12,12',12" Front Screen Detector |
| 14,14',14" Back Screen Detector | |
| 17,17' Light Valve | 16 Optical Chamber |
| 19,19' Film | 18 Controlled Light Source |
| 22 Connector | 20 Sequencer |
| 26 X-ray Tube | 24 X-ray Power Supply |
| 30 Controlled Electric Generators | 28 Field Electrodes |

DESCRIPTION OF THE PREFERRED EMBODIMENT

Figure 1A:
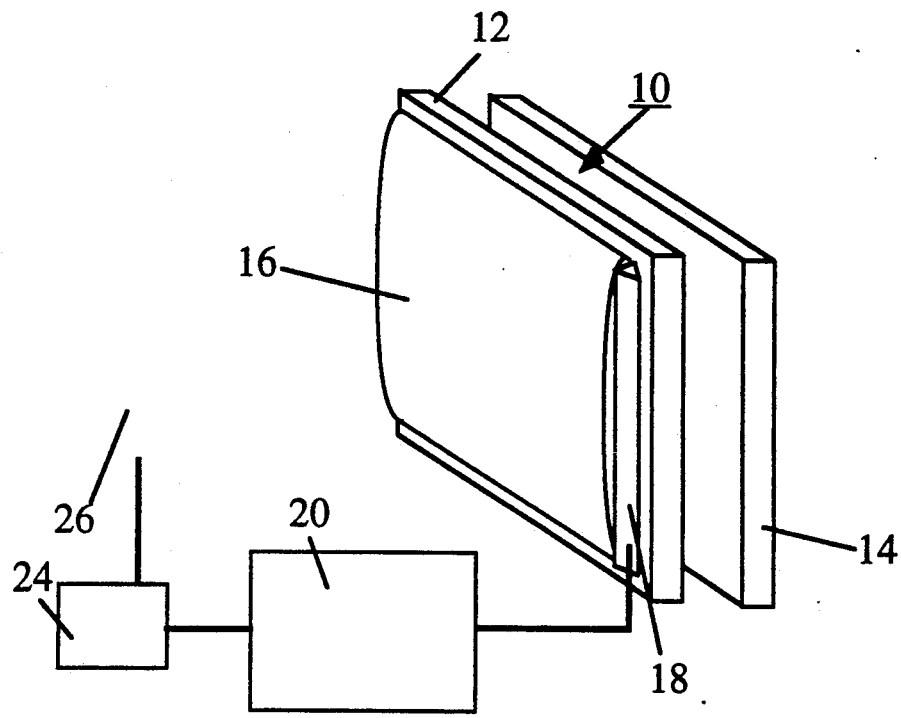
FIG. 1A shows the preferred embodiment of the invention using light to control the response of a storage phosphor screen detector.

The preferred embodiment is illustrated in FIG. 1A. It consists of a cassette 10 and a sequencer 20. An x-ray power supply 24 and an x-ray tube 26 are parts of a medical x-ray system used with the present invention. Cassette 10 consists of a front screen detector 12 and a back screen detector 14 arranged essentially perpendicular to the radiation, a controlled light source 18 is connected to an optical chamber 16 to illuminate the screen essentially uniformly. Screens 12 and 14 are storage phosphor screen area x-ray detectors. Light source 18 has a light spectrum suitable for erasing screen 12. Optical chamber 16 is made of materials with low x-ray attenuation but high optical reflectivity such as plastic coated with a highly diffusely reflecting material. Screens 12 and 14, optical chamber 16 and controlled light source 18 have dimensions so that the overall size of cassette 10 is similar to a conventional film cassette. Sequencer 20 communicates with light source 18 and an x-ray power supply 24 through a connector 22 which can be an electric wire, fiber optic cable, infra-red radiation, or some other suitable means. Sequencer 20 can be implemented with a programmable electronic microprocessor. X-ray power supply 24 provides power for x-ray tube 26. In the embodiment of FIG. 1A light source 18 and optical chamber 16 are arranged to illuminate the front screen. Cassette 10 can be rotated so that the back screen is illuminated.

OPERATION—PREFERRED EMBODIMENT

Figure 2A:
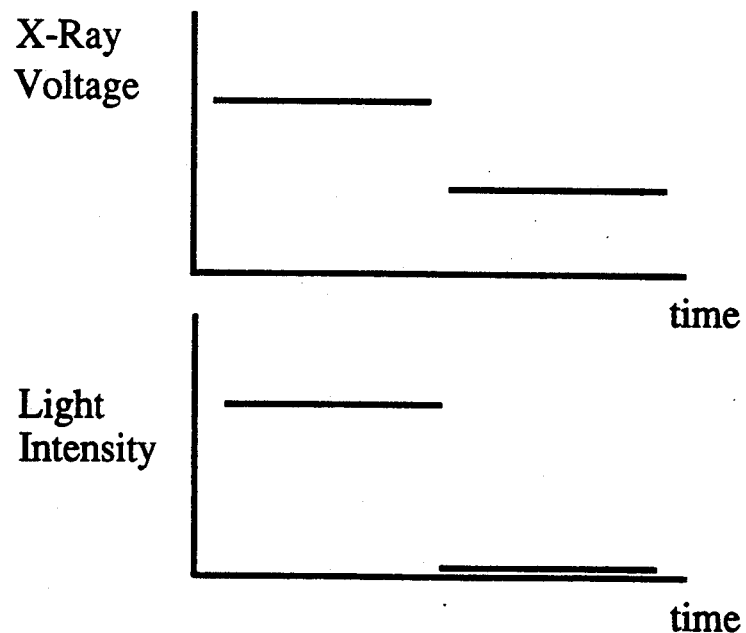
FIG. 2A shows the time waveforms of x-ray tube voltage and light intensity for the cassette of FIG. 1A.

The operation of the preferred embodiment of FIG. 1A may be understood by reference to the time variation of light intensity and x-ray tube voltage in FIG. 2A. Sequencer 20 signals light source 18 to turn on and signals x-ray power supply 24 to produce an exposure with a high voltage (In some implementations, power supply 24 can initiate and control the operation; the results are the same.). Light source 18 has a wavelength and intensity suitable for erasing the latent image. As a result, front screen 12 does not record data while back screen 14 records the high average energy photons produced by the high voltage on x-ray tube 26. At the end of the high voltage exposure, sequencer 20 signals light source 18 to turn off and x-ray power supply 24 to produce a low voltage exposure. At the end of the two exposures, front screen 12 only contains the data from the low x-ray tube voltage exposure while back screen 14 contains the sum of the high voltage exposure plus the small number of low voltage photons transmitted by front screen 12. Screens 12 and 14 may then be read out by a laser scanner as in a conventional storage phosphor screen system and processed using any desired technique.

Light source 18 and optical chamber 16 are constructed so that they produce a high intensity uniform illumination over the surface of front screen 12. The power supply of light source 18 turns it off and on within the period required by the x-ray exposures. Optical chamber 16 is constructed of a material with low x-ray attenuation such as plastic coated with a highly diffusely reflecting material. Since only a uniform illumination is required, the thickness of optical chamber 16 can be made small enough so that the overall thickness of cassette 10 is compatible with conventional film cassettes.

The embodiment of FIG. 1A is preferred for screens made from ordinary materials whose attenuation decreases with energy in the band of interest. Practitioners skilled in the art recognize that attenuation can increase at discrete energies (for example the K-edge). If front screen 12 contains such a material, then it may preferentially absorb high average energy photons. Back screen 14 absorbs the low energy photons. For this case, cassette 10 may be rotated by 180 degrees. Then, optical chamber 16 and light source 18 are connected to back screen 14. The tube voltage and light intensity are the same as in FIG. 2A. At the end of the two exposures, back screen 14 only contains the data from the low x-ray tube voltage exposure while front screen 12 contains the sum of the high voltage exposure plus the small number of low voltage photons detected by it. Screens 12 and 14 may then be read out by a laser scanner as in a conventional storage phosphor screen system and processed using any desired technique.

THEORY OF OPERATION—PREFERRED EMBODIMENT

The function of the present invention is to measure the x-ray flux transmitted through the object by photons with different energies. The invention achieves better performance than previous approaches by combining x-ray source spectrum switching and a layered cassette with two new elements: an element to control the response of the detector screens and a sequencer to synchronize the source and the control element. The sequencer adjusts the control element so that the relative response of one screen to the source spectrum with low average energy is enhanced while the relative response of the other screen to the high average energy spectrum is enhanced. The screen chosen for enhanced response is predetermined to enhance the selectivity of the passive layered cassette. As described previously, depending on the attenuation function of the front screen, either the front or back screen preferentially detects low energy photons. The other screen then preferentially detects high energy photons. The control signals produced by the sequencer are predetermined so that the response to low and high average energy source spectra by the corresponding screens of the passive layered cassette are enhanced. The active cassette thus gives greater selectivity than either source spectrum switching or a passive cassette. Because the selectivity is achieved by controlling the response, no mechanical motion is required. The control elements and screen detectors have dimensions so that the active cassette remains compatible with film cassette holders.

The control of response involves erasing or decreasing the response to some of the x-ray radiation. Practitioners skilled in the art of x-ray imaging will realize that this may increase the quantum noise in the measurements. The surprising result of the present invention is that the increased noise in the individual measurements results in substantially lower noise in the final processed data. The previously cited paper by Alvarez and Macovski shows that the noise in the processed energy spectrum information depends on the product of two factors: (1) the noise in the individual measurements, and (2) a quantity related to the difference in average energies. With erasing, the noise in the measurements increases but the difference in average energies also increases. The result is that the decrease in noise due to the larger difference in average energy is much larger than the increase due to erasing detected photons. This theoretical result was verified experimentally as will be described in the next section.

The preferred embodiment uses a photostimulated luminescence storage phosphor screen. The general operation of x-ray imaging systems using these screens is described in U.S. Pat. No. 3,859,527 (1975) issued to G. W. Luckey. Storage phosphor screens function as a re-usable x-ray film. They are used in a cassette, similar to a film cassette, during medical examinations to acquire a an x-ray image. The image is stored as a latent image in the material of the screen (also known as a stimulable phosphor screen). After the examination, the screens are removed from the cassette and scanned in a laser scanner. The scanner reads out the latent image from the screen and converts it to electronic digital signals. The digital signals are processed by a computer, then viewed on photographic film or on a cathode ray tube computer console. After the latent image is read out by the laser scanner, the screen can be erased and re-used. Storage phosphor screens have excellent quantitative properties. They have wide dynamic range (approximately 1000 to 1) and are linear and stable. Storage phosphor screen detectors have no inherent energy selective capability. They must be used in an energy selective detector apparatus.

The function of the present invention with storage phosphor screen detectors depends on the properties of storage phosphor materials. The screens contain storage phosphor material coated on a sheet. A storage phosphor stores a latent x-ray image as electrons trapped in high energy metastable (i.e. long term stable) sites. During the x-ray examination, x-ray photons interact with the phosphor creating high energy electrons some of which are trapped in the metastable sites. These trapped electrons are the latent image. The electrons can be released from the metastable sites by shining light on the phosphor. When they are released, they emit light in proportion to the x-ray flux incident on the screen. The image is read out by scanning a focused laser beam over the surface of the screen and measuring the resultant emitted light.

Light with a properly chosen wavelength must be used to read out or erase the latent image. The light photons need to have sufficient energy to release the trapped electrons but not enough energy to raise ground state electrons to the metastable states. The energy is related to their wavelength by Planck's relation. Before use, the screen is exposed to uniform light with this wavelength. This light releases essentially all the trapped electrons from past exposures leaving a blank screen ready to store a new image. An important fact for the present invention is that the erasing process can work during the x-ray exposure. Then there will be two competing processes: the x-ray photons populating the metastable sites and the light illumination releasing them. If the light has a sufficiently high intensity, essentially no latent image will remain.

Therefore, by using light, one can select which of several x-ray exposures is recorded on a screen. This capability is combined with the operation of a layered detector energy selective cassette in the present invention. X-ray photons with one energy spectrum are incident on a layered cassette. One of the layers is simultaneously exposed to erasing light whose wavelengths are chosen as discussed above. This layer will thus not record data from this x-ray exposure. A second x-ray exposure with a different source spectrum may then be made without the light source off. The second x-ray exposure will be the only data recorded on this layer. The other layer (or layers) are not exposed to light during measurement process. They will record the same data as in an ordinary passive layered cassette. By using source spectra with large differences in average energy, such as by using large changes in x-ray tube voltage, the detector can record the x-ray fluxes transmitted through the object with much larger differences than passive layered detector cassettes. Because of the inherent selectivity of passive layered detectors, the detected spectra will also have larger differences than simply recording the transmitted flux with the source spectra.

EXPERIMENTAL RESULTS

The improved performance of the present invention over prior art was verified experimentally. The response of a storage phosphor screen in a prior art passive layered cassette and in an active cassette constructed as illustrated in FIG. 1A was measured. The passive cassette was exposed to a single x-ray exposure from an x-ray tube operating at 60 kilovolts (kV) while two exposures of 90 and 55 kV were used with the active cassette. By measuring the transmission through 5 different thicknesses of a known material, the average energies of the detected spectra of the two screens in each cassette design were measured. Then the signals from the x-ray flux transmitted through an object as well as a quantity proportional to the absorbed dose of the object were measured. The results are summarized in Table 1.

TABLE 1

| Experimental Results Comparing Active and Passive Cassettes ||||||||||
| Active Cassette ||||||||||
| Ave. Energy Front (keV) | Ave. Energy Back (keV) | $m_{11}$ (cm²/gm) | $m_{12}$ (cm²/gm) | $m_{21}$ (cm²/gm) | $m_{22}$ (cm²/gm) | $I_1$ (mV) | $I_2$ (mV) | Dose (mV) | $\sigma_{active}2$ |
| 32 | 42 | 3.31 | 0.234 | 1.57 | 0.199 | 17 | 80 | 321 | .036 |
| Passive Cassette ||||||||||
| Ave. Energy Front (keV) | Ave. Energy Back (keV) | $m_{11}$ (cm²/gm) | $m_{12}$ (cm²/gm) | $m_{21}$ (cm²/gm) | $m_{22}$ (cm²/gm) | $I_1$ (mV) | $I_2$ (mV) | Dose (mV) | $\sigma_{passive}2$ |
| 37 | 40 | 2.21 | 0.213 | 1.79 | 0.204 | 68 | 37 | 271 | .38 |

A quality factor for the performance of an energy selective detector may be defined as $$Q = \frac{1}{\sigma^2 \text{Dose}}$$

where $\sigma^2$ is the variance of the processed energy information and Dose is the total x-ray patient dose used to measure the energy selective information. Note that the quality factor increases when either the noise or dose decreases. Smaller noise means that more subtle features in the image can be distinguished. Dose reduction is always a positive improvement especially in medical radiography.

The previously cited paper by Alvarez and Macovski shows that the noise variance $\sigma^2$ is $$\sigma^2 = \frac{\sigma_2{}^2 m_{12}^2 + \sigma_1{}^2 m_{22}^2}{(m_{11}m_{22} - m_{12}m_{21})^2}$$

where $\sigma_1{}^2$ and $\sigma_2{}^2$ are the variances in the individual energy spectrum measurements and $m_{ij}$ ($i,j=1,2$) are related to the average energy of the effective spectra. The variances are inversely proportional to their average values so $\sigma_1{}^2 = 1/I_1$ and $\sigma_2{}^2 = 1/I_2$.

The data in TABLE 1 can be used to calculate the ratio of quality factors of the present invention and previous passive cassettes $$\frac{Q_{active}}{Q_{passive}} = \frac{\sigma^2_{passive}}{\sigma^2_{active}} \frac{\text{Dose}_{passive}}{\text{Dose}_{active}}.$$

The result is that the ratio for our experiments is approximately 9. The invention gives 9 times better (i.e. less) noise for the same patient dose as prior art. Larger improvements may be possible by optimizing the source spectra and detectors.

DESCRIPTION—FIGS. 1B AND 1C

The response of the detectors can be controlled in many different ways. The preferred embodiment of FIG. 1A uses light with storage phosphor screens. Other embodiments use electric fields with storage phosphor screens as illustrated in FIG. 1B, and light valves with intensifying screens and films as illustrated in FIG. 1C.

Figure 1B:
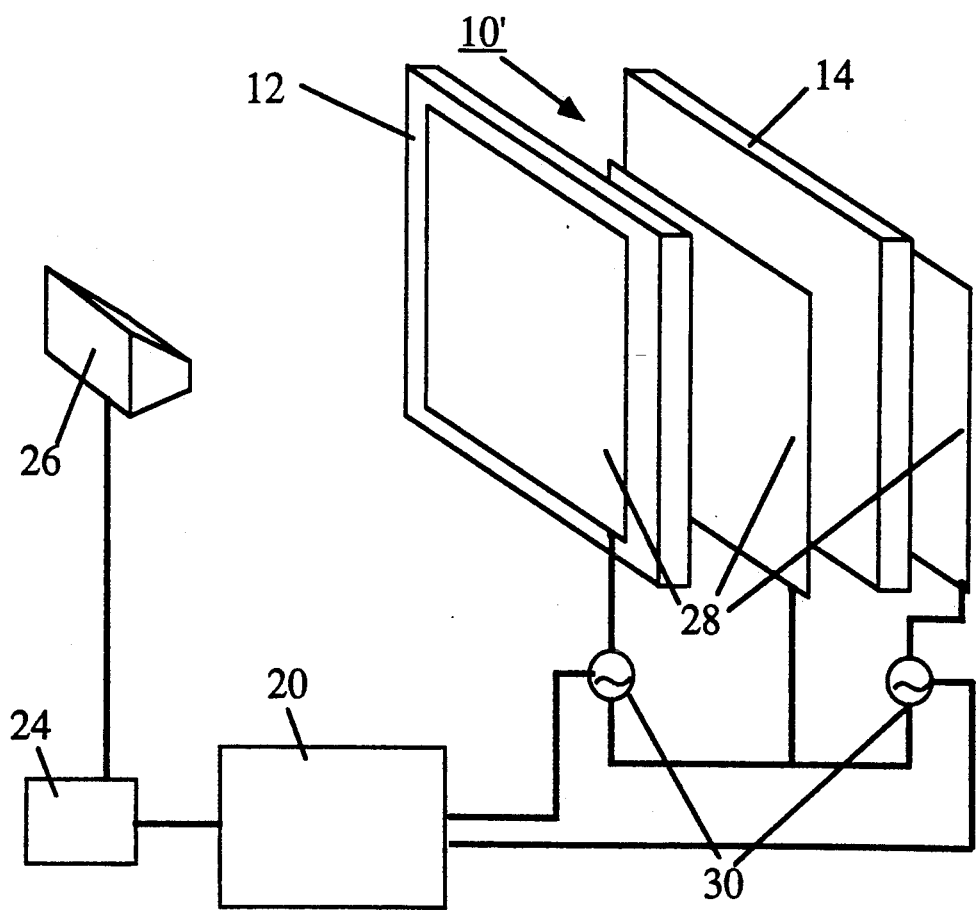
FIG. 1B shows an embodiment of the invention using electric field control of the response of a storage phosphor screen detector.

The embodiment in FIG. 1B consists of an electric field control cassette 10' and sequencer 20. Cassette 10' consists of a front screen 12' and a back screen 14' arranged essentially perpendicular to the radiation and a set of controlled electric generators 30 connected to a set of field electrodes 28 to create electric fields in screens 12' and 14'. Screens 12' and 14' are storage phosphor screen area x-ray detectors. Field electrodes 28 are made from material with low x-ray attenuation but high electrical conductivity such as 50 micrometer thick aluminum sheet. Sequencer 20 communicates with electric generators 30 and x-ray power supply 24 through connector 22. Screens 12' and 14' and field electrodes 28 have dimensions so that the overall size of cassette 10' is similar to a conventional film cassette.

Figure 1C:
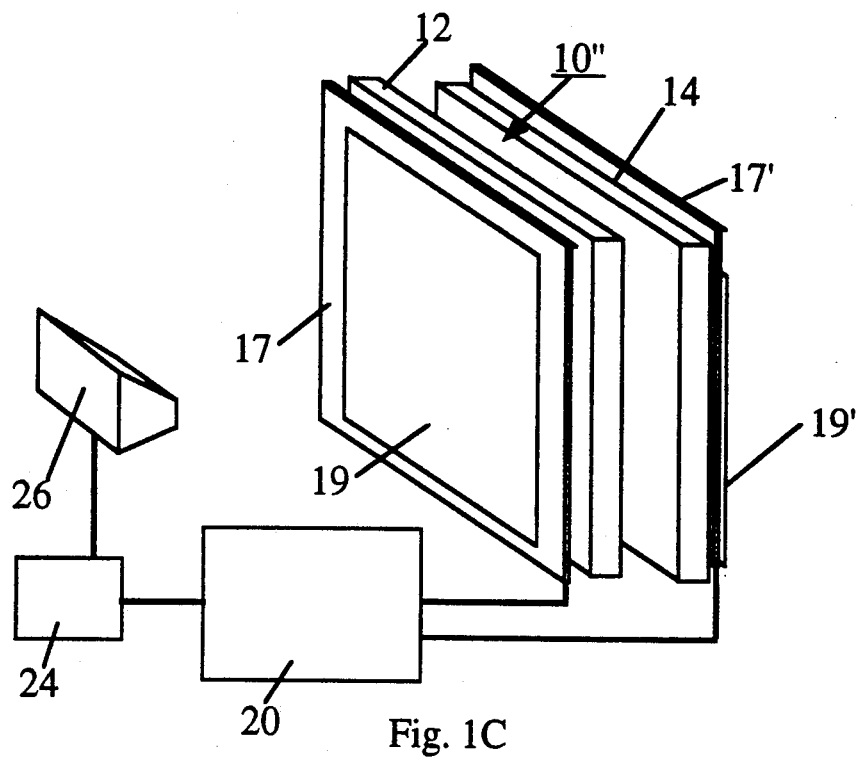
FIG. 1C shows an embodiment of the invention using a light valve with a film/intensifying screen detector.

The embodiment in FIG. 1C uses conventional intensifying screen and film detectors. It consists of a light valve control cassette 10" and sequencer 20. Cassette 10" consists of a front intensifying screen 12" and a back intensifying screen 14" arranged essentially perpendicular to the radiation, light valves 17 and 17', and light sensitive film sheets 19 and 19'. Light valves 17 and 17' control the amount of light produced by screens 12" and 14" that reach light sensitive film sheets 19 and 19'. Screens 12" and 14" are conventional x-ray intensifying screens that emit visible light when struck by x-ray radiation. Film sheets 19 and 19' can be conventional silver halide film. Light valves 17 and 17' have a light transmission that is controlled by an external signal. They can be sheets of liquid crystal light valve. Sequencer 20 communicates with light valves 17 and 17' and x-ray power supply 24 through connector 22. Screens 12" and 14", light valves 17 and 17', and film sheets 19 and 19' have dimensions so that the overall size of cassette 10" is similar to a conventional film cassette.

THEORY OF OPERATION—FIG. 1B ELECTRIC FIELD CONTROL

Electric fields may also be used to control the response of some storage phosphors. This is shown in the papers: "The effect of alternating electric fields on the excitation of a strontium sulfide phosphor," by W. Low, I. T. Steinberger, and E. A. Braun, J. Optical Soc. Amer., Vol. 44, 1954, pp. 504–505 and "Gudden-Pohl and memory effects in an infra-red stimulated phosphor," I. T. Steinberger, E. A. Braun, A. Alexander, J. Phys. Chem. Solids, Vol. 3, 1957, pp. 133–140. These papers describe experiments where the phosphor is subject to electric fields during the exposure to high energy radiation. The physical explanation for this effect is not well understood but it is an experimental fact. The electric fields enhance the signal later read out from the phosphor. This is the opposite of the light control signal of FIG. 1A but it can still be used to improve the performance of an active cassette.

OPERATION—FIG. 1B ELECTRIC FIELD CONTROL

Figure 2B:
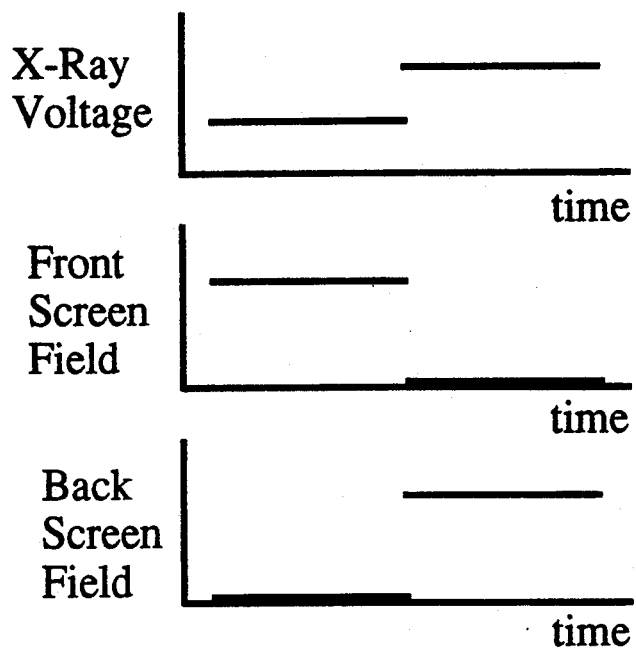
FIG. 2B shows the time waveforms of x-ray tube voltage and electric field magnitude for the cassette of FIG. 1B.

The operation of the embodiment of FIG. 1B may be understood by reference to the time variation of electric field and x-ray tube voltage in FIG. 2B. Sequencer 20 signals electrical generators 30 to place a high field on back screen 14 and a low field on front screen 12 and signals x-ray Power Supply 24 to produce an exposure with a high voltage. As a result, the response of back screen 14 is enhanced while the response of front screen 12 is not changed during the first exposure. At the end of the high voltage exposure, sequencer 20 signals electrical generators 30 to place a high field on front screen 12 and a low field on back screen 14 and signals x-ray Power Supply 24 to produce an exposure with a low voltage. At the end of the two exposures, front screen 12 contains the enhanced response from the low x-ray tube voltage exposure plus the ordinary response from the high voltage exposure. Back screen 14 contains the sum of the enhanced response from the high voltage exposure plus the ordinary response of the low voltage exposure. If the enhancement of response due to the fields is large, then the signal from front screen 12 will essentially be due to the low voltage exposure while the response of back screen 14 will be due principally to the high voltage exposure. Screens 12 and 14 may then be read out by a laser scanner as in a conventional storage phosphor screen system and processed using any desired technique.

Field electrodes 28 are made from any material with high electrical conductivity but low x-ray attenuation, for example 50 micrometer thick aluminum foil. For some phosphors, the change of the response is enhanced by using an oscillating AC field. In this case the signals in FIG. 2B are the amplitude of the oscillation. For front screen 12 with an absorption edge, the electric field signals may be applied to the reverse screens.

THEORY OF OPERATION—FIG. 1C INTENSIFYING SCREEN/FILM

The response of conventional film/intensifying screen x-ray image detectors can be controlled by using a light valve to control the transmission of light from the screen to the film. If no light reaches the screen then the x-ray flux will not be recorded. An example of a light valve is a sheet of liquid crystal material applied to the intensifying screen. In one state, this sheet transmits light and in another state it absorbs light. The state is controlled by electric fields applied to the liquid crystal sheet. The liquid crystal light valve is made of material that transmits x-ray radiation.

OPERATION—FIG. 1C INTENSIFYING SCREEN/FILM

Figure 2C:
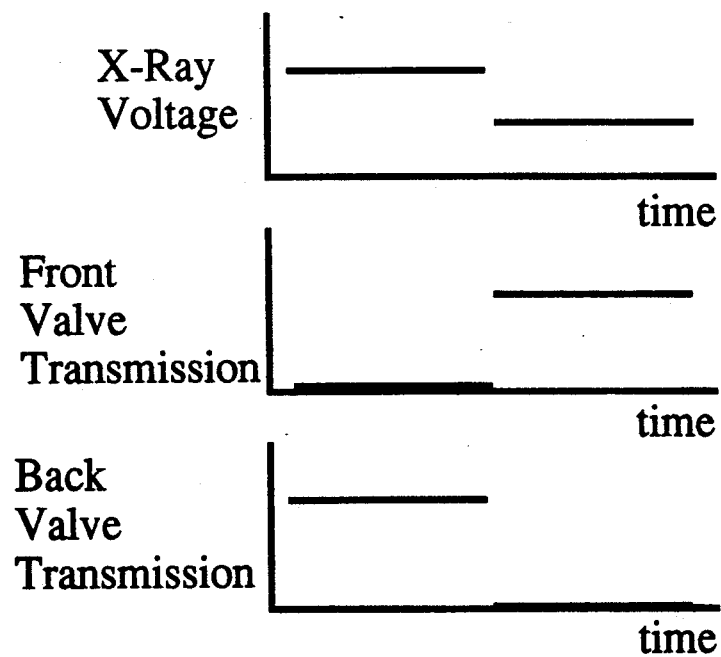
FIG. 2C shows the time waveforms of x-ray tube voltage and light valve transmission for the cassette of FIG. 1C

The operation of the embodiment of FIG. 1C may be understood by reference to the time variation of light transmission and x-ray tube voltage in FIG. 2C. Sequencer 20 signals a front screen light valve 17 to go into a low transmission and a back screen light valve 17' to go into high transmission state, then signals x-ray Power Supply 24 to produce an exposure with a high voltage. As a result, front screen film 19 does not record data while back screen film 19' records the high average energy photons produced by the high voltage on x-ray tube 26. At the end of the high voltage exposure, sequencer 20 signals front screen light valve 17 to go into a high transmission state and a back screen light valve 17' to go into a low transmission state, then signals x-ray Power Supply 24 to produce an exposure with a low voltage. At the end of the two exposures, front screen film 19 only contains the data detected by front screen 12 from the low x-ray tube voltage exposure while back screen film 19' contains the data detected by back screen 14 from the high voltage exposure. Films 19 and 19' may be scanned by a conventional film scanner and their data processed using any desired technique.

DESCRIPTION—FIGS. 2A, 2B, AND 2C

These figures illustrate the time waveforms of the control signals produced by sequencer 20. FIG. 2A shows the signal for cassette 10 with light control of response. They are an x-ray tube voltage signal that indicates the anode voltage applied to x-ray tube 26 and a light intensity indicating the intensity produced by light source 18. FIG. 2B shows the signals for cassette 10' with electric field control. They are an x-ray tube voltage signal and electric field magnitudes. In some cases the electric fields are alternating (AC). Then the electric field signals are the amplitude of the oscillation. FIG. 2C shows the signals for cassette 10" with light valve control of response. They are an x-ray tube voltage signal and a light valve transmission signal.

SUMMARY, RAMIFICATIONS, AND SCOPE

The reader will see that the active energy selective x-ray image detector system of the invention provides higher quality data than prior art without mechanical motion in a cassette whose dimensions are compatible with the film cassettes used in medical x-ray equipment.

Although the description above contains many specificities, these should not be construed as limiting the scope of the invention but as merely providing illustrations of some of the presently preferred embodiments of this invention. For example: heat can also be used to erase some storage phosphors and controlled heating elements can be included within the active cassette; the control signal can be adjusted so as not to erase completely the storage phosphor screen but record a fraction of the image producing data representing a weighted sum of the spectra that may be useful in some applications of energy spectrum information; an x-ray absorbing filter can be placed between detectors; more than two detectors can be used; etc.

Thus the scope of the invention should be determined by the appended claims and their legal equivalents, rather than by the examples given.

"This invention was made with Government support under Grant 1 R43 CA55430-01 awarded by the National Institutes of Health. The Government has certain rights in this invention."

What is claimed:

1. Energy discriminating radiation detector apparatus for selectively recording two sequentially incident fluxes of x-ray radiation, said apparatus comprising:
   (a) two planar screen x-ray radiation detectors arranged parallel to each other,
   (b) controller means for controlling the response of said detectors,
   (c) sequencer means for synchronizing the controlled response of said detectors with said sequentially incident fluxes of x-ray radiation,
       wherein detector response of each of said detectors to a predetermined energy spectrum is selectively enhanced.

2. The apparatus of claim 1 wherein said planar screen x-ray radiation detectors comprise storage phosphor screen detectors.

3. The apparatus of claim 2 wherein said means for controlling the response of said storage phosphor screen x-ray radiation detector comprises a controlled light source and optical chamber means to distribute light from said controlled light source over one of said storage phosphor screen detectors.

4. The apparatus of claim 2 wherein said means for controlling the response of each of said storage phosphor screen detectors comprises a controlled electrical generator connected to electrically conducting electrode means for producing electric fields in the storage phosphor screen.

5. The apparatus of claim 1 wherein said planar screen detectors comprise film and intensifying screen x-ray radiation image detectors and said means for controlling the response of each of said detectors comprise light valve means interleaved between detector film and intensifying screen for controlling the amount of light energy from said intensifying screen reaching said detector film.

6. An imaging method comprising the steps of:
   (a) directing two fluxes of x-ray radiation sequentially through an object to be imaged, said fluxes having different energy spectra;
   (b) detecting x-ray radiation emergent from said object by a radiation detector comprising:
       two planar screen detectors arranged parallel to each other, means for controlling the response of said detector, sequencer means for synchronizing the controlled response of said planar screen detectors with said x-ray radiation emergent from said object;
   (c) controlling the response of said planar screen detectors so the response of a predetermined planar screen detector to each of the fluxes of x-ray radiation is selectively enhanced;
   (d) reading data from said planar screen detectors; and,
   (e) processing said data to produce a representation of the internal structure of said object.

7. The method of claim 6 wherein said planar screen detectors comprise storage phosphor screen detectors.

8. The method of claim 7 wherein said means for controlling the response of said storage phosphor screen x-ray radiation detectors comprises a controlled light source and optical chamber means to distribute light from said controlled light source over one of said storage phosphor screen detectors.

9. The method of claim 6 wherein said planar screen detectors comprise film and intensifying screen x-ray radiation image detectors and said means for controlling the response of each of said detectors comprise light valve means interleaved between detector film and intensifying screen for controlling the amount of light energy from said intensifying screen reaching said detector film.

10. The method of claim 7 wherein:
(a) said means for controlling the response of said storage phosphor screen detectors comprises means for substantially erasing the information stored on the storage phosphor screen detector closest to said object;
(b) said controlled response comprises erasing the information from the first of said fluxes of x-ray radiation from the detector closest to said object;
(c) the first of said two fluxes of x-ray radiation has a higher average energy than the second of said two fluxes; and,
(d) x-ray absorption of said detector closest to said object is substantially lower at the average energy of first of said two fluxes than at the average energy of second of said two fluxes.

11. The method of claim 7 wherein:
(a) said means for controlling the response of said storage phosphor screen detectors comprises means for substantially erasing the information stored on the storage phosphor screen detector farthest from said object;
(b) said controlled response comprises erasing the information from the first of said fluxes of x-ray radiation from the detector farthest from said object;
(c) the first of said two fluxes of x-ray radiation has a higher average energy than the second of said two fluxes; and,
(d) x-ray absorption of said detector farthest from said object is substantially lower at the average energy of first of said two fluxes than at the average energy of second of said two fluxes.

12. The method of claim 7 wherein said means for controlling the response of said storage phosphor screen detector comprises controlled electrical generators connected to electrically conducting electrode means for producing electric fields in said storage phosphor screen detectors.

* * * * *